United States Patent [19]
Gundersen et al.

[11] 4,326,425
[45] Apr. 27, 1982

[54] DRIVE CONTROL ARRANGEMENT FOR SWING ARM MATERIAL SAMPLER

[75] Inventors: Ray S. Gundersen, Salt Lake County; Ronald J. Colledge; Roy H. Jenkins, both of Davis County; Michael Crook, Salt Lake County, all of Utah

[73] Assignee: Sverdrup & Parcel and Associates, Inc., St. Louis, Mo.

[21] Appl. No.: 195,140

[22] Filed: Oct. 8, 1980

[51] Int. Cl.³ .............................................. G01N 1/20
[52] U.S. Cl. ................................................. 73/863.53
[58] Field of Search ........... 73/863.53, 863.54, 863.55, 73/863.91, 864.31

[56] References Cited
U.S. PATENT DOCUMENTS

| 2,495,944 | 1/1950 | Pletta et al. | 73/863.53 |
| 2,977,800 | 4/1961 | Jordison | 73/423 |
| 3,198,017 | 8/1965 | Taylor et al. | 73/421 |
| 3,252,328 | 5/1966 | Huntington | 73/863.54 |
| 3,541,862 | 11/1970 | Jordison | 73/423 |
| 3,875,803 | 4/1975 | Clewlow | 73/423 R |
| 3,908,464 | 9/1975 | Flinchbaugh | 73/864.31 |
| 4,215,579 | 8/1980 | Hines et al. | 73/424 |

Primary Examiner—S. Clement Swisher
Attorney, Agent, or Firm—Gravely, Lieder & Woodruff

[57] ABSTRACT

A drive control arrangement for a material sampling apparatus in which the sampling bucket is operatively carried on a swing arm for movement through a stream of material when in the now sampling position and in a reverse direction back through the stream in a sample cutting position so that the sample can be dumped and directed to processing apparatus ancillary to the sampling apparatus. The apparatus is placed under the drive control arrangement for hydraulic and electrical systems which control the sequence of movements of the swing arm and the sampling bucket and the directing of the sample when dumped from the bucket.

8 Claims, 10 Drawing Figures

DRIVE CONTROL ARRANGEMENT FOR SWING ARM MATERIAL SAMPLER

BACKGROUND OF THE INVENTION

1. Field of the Invention

This invention is directed to drive control apparatus for obtaining samples of material, such as coal from a moving stream of crushed coal, for the purpose of analysis of the characteristics of the material.

2. Description of the Prior Art

The need for obtaining samples of various materials, coal being one, from a moving stream has been known, and various arrangements of apparatus have been put forth to accomplish that result. The purpose of coal sampling apparatus is to extract selected samples which are representative of the total flow of the coal as it is delivered from a primary crusher, and to deliver the samples to secondary crusher means associated with means to analyse certain characteristics of the coal.

Coal samplers of the type generally incorporating a swing arm are provided with a bucket which is moved through a falling stream of crushed coal. In this category of prior art are found U.S. Pat. Nos. Jordison 2,977,800 of Apr. 4, 1961; Taylor et al 3,198,017 of Aug. 3, 1965; Jordison 3,541,862 of Nov. 24, 1970; and Clewlow 3,875,803 of Apr. 8, 1975. A portable type coal sampler has been disclosed in the Hines et al U.S. Pat. No. 4,215,579 of Aug. 5, 1980.

BRIEF DESCRIPTION OF THE INVENTION

The present invention is directed to the drive control for material sampling apparatus of compact construction in which a sampling bucket achieves the sampling from a falling stream of material quickly and by taking a minimum quantity of material from the falling stream. The present disclosure will be given in relation to coal without imposing limitations as to the sampling of other materials.

It is a general object of the present invention to provide apparatus readily adaptable to a coal crushing station with minimum structural problems and having a reliable high speed sampling operation.

A further object of the present invention is to provide a drive control arrangement for a coal sampling apparatus which is automatic in performing a sampling operation in the movement from the home position of the sampler bucket through the falling stream of coal and then back through the stream to cut a sample which is discharged at the home position.

A preferred embodiment of the present drive control arrangement comprises a frame which fits over the conveyor head pulley delivering the crushed coal to a suitable elevation where a free falling stream is established; a swing arm operably carried in the frame; a sampling bucket operably carried by the swing arm and movable by the arm in an arcuate path that carries the bucket through the falling coal stream; control means for moving the swing arm at a predetermined speed in directions from a home position for the bucket through the coal stream and back to the home position; other control means for positioning the bucket in a position to pass through the coal stream without cutting a sample and to a position for cutting a sample from the coal stream, and back to a position to dump the sample; and sample directing means movable between a position out of the path of bucket movement during the sample cutting operation and a position for directing the coal sample out of the apparatus upon the bucket moving to dump the coal sample.

The present embodiment is unique in relation to the prior art in the design of the apparatus to eliminate bulky structure and in the operation in which the overhead swing arm that moves in a vertical arc carries the sampling bucket down through the coal stream in a non-cutting position and then up through the coal stream to obtain a non-biased sample which is then dumped. The dumped sample is directed to a sample feeder and crusher for subsequent analysis.

BRIEF DESCRIPTION OF THE DRAWINGS

A presently preferred embodiment of the sampler apparatus is disclosed in the accompanying drawings, wherein.

DETAILED DESCRIPTION OF THE PREFERRED EMBODIMENT

Figure 1:
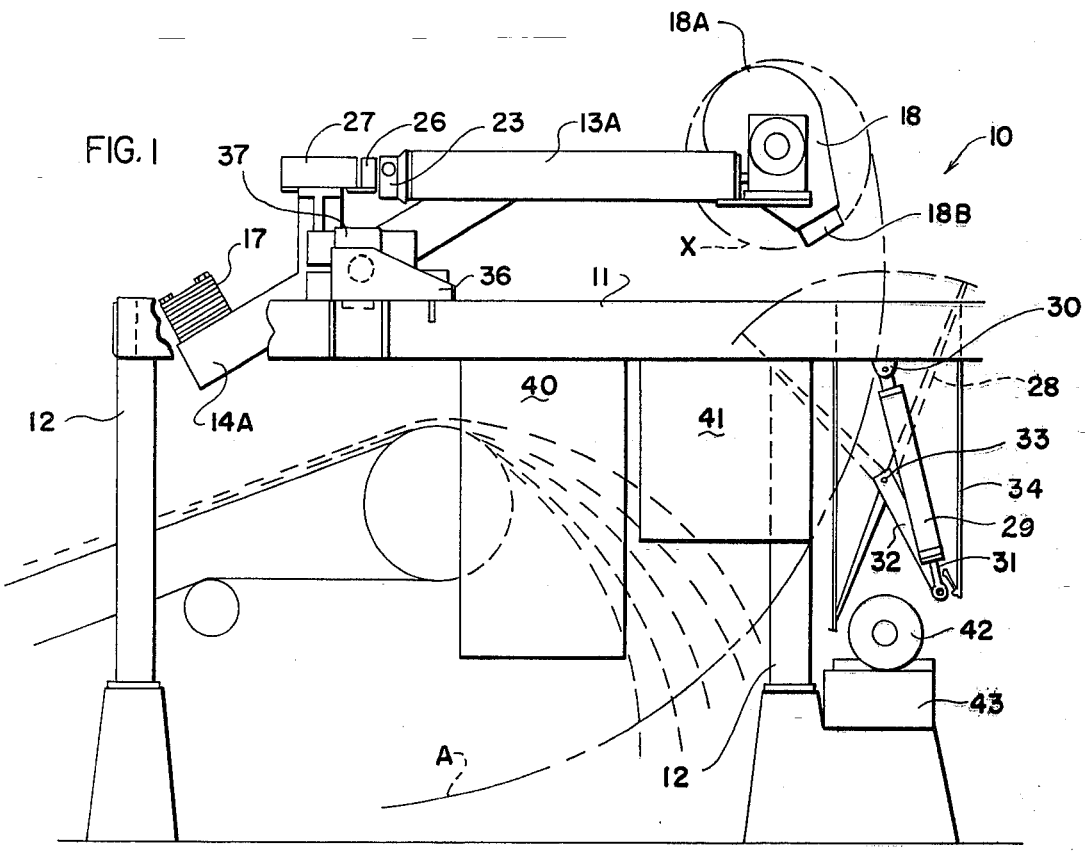
FIG. 1 is a side elevation of the sampler apparatus with the bucket in dump position, and to illustrate the various components and control provisions.

The swing arm coal sampler apparatus is shown generally at 10 and comprises a horizontal frame 11 supported on vertical pillars 12. A swing arm assembly is pivotally mounted on the horizontal frame 11 and comprises horizontal arm portions 13A and 13B and angularly directed arm portions 14A and 14B connected to a transverse shaft 15 carried in suitable bearings 16 attached to the frame 11. The angularly directed arm portions 14A and 14B carry a suitable counterweight 17 made up of a plurality of plates which may be removed or added in order to allow the swing arm assembly to move with a minimum unbalance on each side of the pivot shaft 15. The outer end of the swing arm portions 13A and 13B carry the sampling bucket 18 which is pivotally mounted between the arm portions so that it may be free to rotate 360°, as will be presently pointed out. The bucket 18 is shown in its normal unloaded position where it has ended at the home position after unloading the coal sample, thereby being in a position to move through a subsequent sampling operation.

Figure 2:
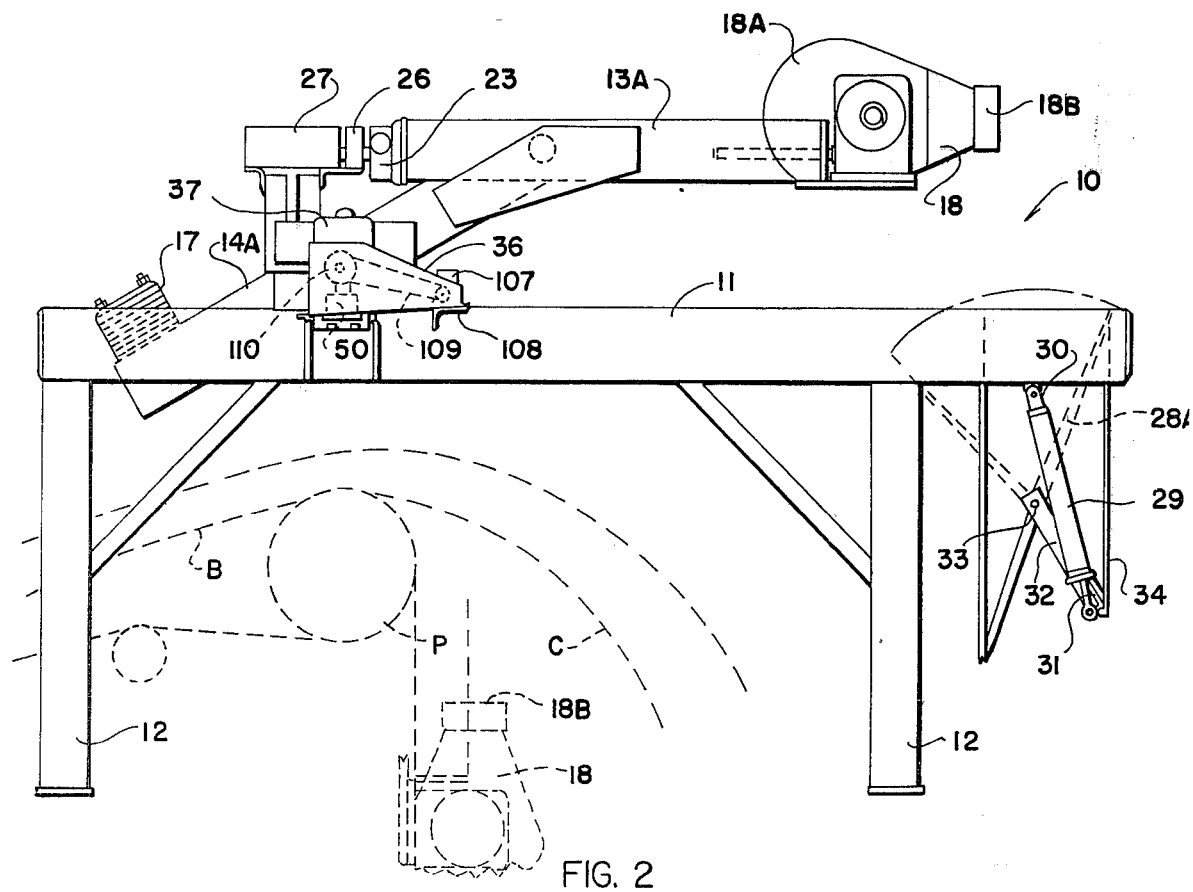
FIG. 2 is a schematic elevational view of only so much of the apparatus as is necessary to show its relationship to the head pulley for the conveyor which lifts the crushed coal and creates the free falling stream thereof.

FIG. 2 is a somewhat diagrammatic view of the assembly 10 to illustrate the relationship between the positions of the horizontal frame members 11 and vertical columns 12 and the conveyor belt B which passes around a suitable head pulley P so as to deliver a stream of crushed coal C in a free fall off the end of the pulley P. In this view, the bucket 18 is free to rotate through 360° as illustrated by the circular path X. Since the swing arm portions 13A and 13B pivot about the axis of the horizontal shaft 15, the sampling bucket 18 is movable through an arcuate path A so that the bucket 18 passes through the free falling stream of coal while in a position to present its circular surface 18A into the coal stream thereby reducing to a minimum the amount of disturbance in the falling stream of coal.

Figure 3:
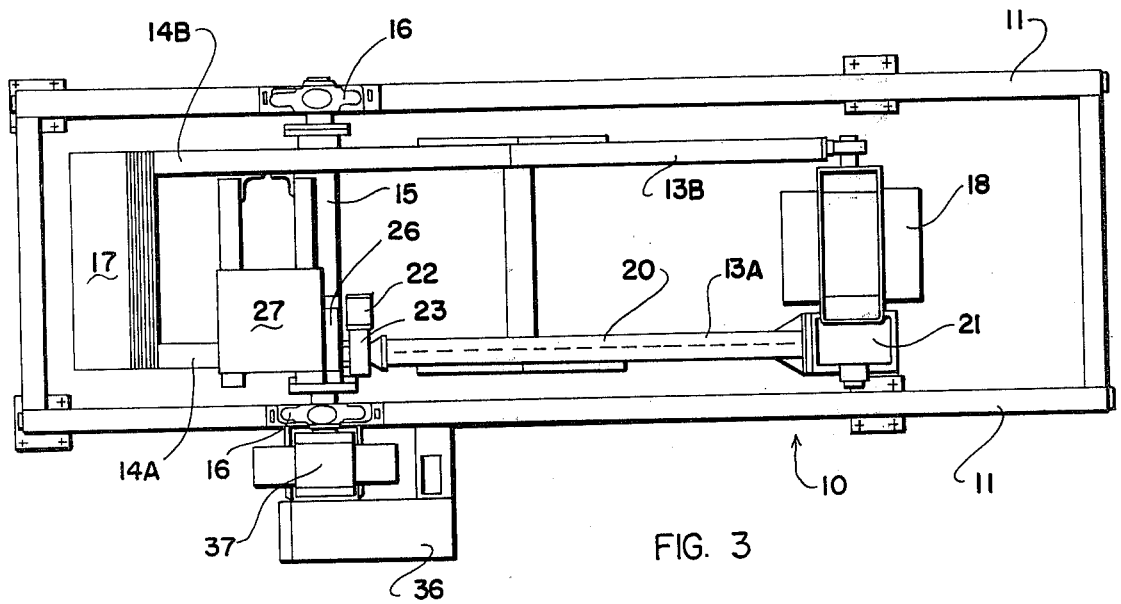
FIG. 3 is a top plan view of the sampler apparatus with the bucket in the non-spill position.

Turning now to FIG. 3, it can be seen in the plan view that the swing arm 13A differs from its cooperating arm 13B in that it is hollow so as to enclose a drive shaft 20 which is connected at the outer end into a suitable gear box 21 for rotating the sampling bucket 18. The inner end of the swing arm portion 13B is connected at a suitable hydraulic motor 22 which drives gear means operatively mounted in housing 23. The housing 23 has an output shaft connected into a geared drive means in housing 26 for rotating switch means 27A in housing 27.

It can be seen in FIGS. 1 and 2 that the frame structure 11 supports a directing means 28 which is movable between extended and retracted positions by means of a hydraulic actuator cylinder 29 which is attached at 30 to the frame 11 and has its operating piston rod 31 connected to the crank arm 32 attached to the directing means 28 adjacent the pivot shaft 33. A shield structure 34 is suspended from the frame 11 and partially encloses the means 28 so that the coal sample dumped from the sampling bucket 18 will be substantially confined by the shield 34. The bottom of the shield 34 is open so that the coal sample will be directed to auxiliary equipment associated with the sampler apparatus such as a take away conveyor (not necessary to show).

Referring again to FIG. 1 and to FIG. 3, it can be seen that a housing 36 is positioned so as to be adjacent the pivot shaft 15 for the swing arm portions 14A and 14B. The housing 36 is adjacent a suitable motor means 37 which is a rack and pinion apparatus, such as a hydraulic actuator made by Hydra Power, Inc. and disclosed in Meyer et al U.S. Pat. No. 3,979,909 of Sept. 14, 1976. The rack and pinion apparatus 37 is operative to oscillate the shaft 15 which swings the arms 13A and 13B through substantially 90° between its home position shown in full line in FIG. 2 and in broken line which represents the bottom position.

Figure 4A:
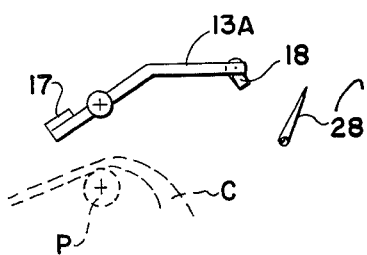
FIG. 4A is a diagrammatic view of the motion sequence at the home position.
Figure 4B:
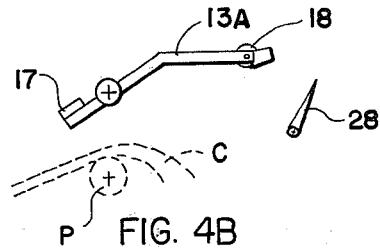
FIG. 4B is a diagrammatic view of the swing arm and bucket motion prior to the initial swing through the coal stream.
Figure 4C:
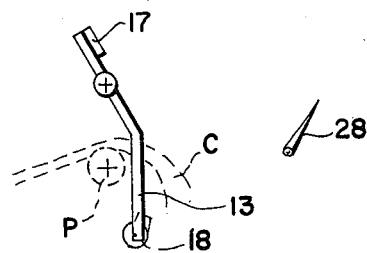
FIG. 4C is a diagrammatic view of the position of the swing arm and sampling bucket prior to the movement to cut a sample.
Figure 4D:
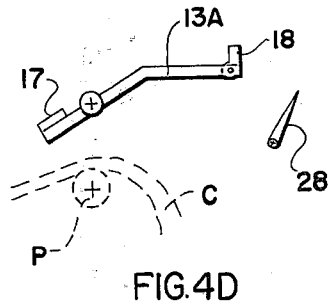
FIG. 4D is a diagrammatic view of the movement of the swing arm and sampling bucket at the home position of the swing arm where the sample directing means begins its movement into position.
Figure 4E:
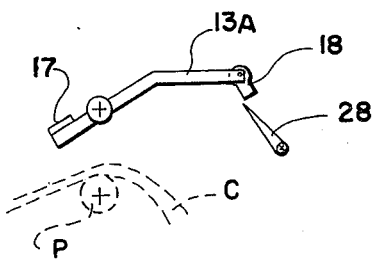
FIG. 4E is a diagrammatic view of the sampling bucket discharging its sample.

Attention will now be directed to the views of FIGS. 4A through 4E which depict the motion sequence of the swing arm, the sampling bucket and the directing means 28. FIG. 4A illustrates diagrammatically the home position of the swing arm, and the sample dump position for the bucket 18, as well as the retracted position of the means 28 so as to remove it from the arcuate path A traversed by the bucket 18. In FIG. 4B, the swing arm is about to move in a downward or clockwise direction and the sampling bucket 18 is shown to be rotated so that its circular surface 18A is in proper position to pass through the free falling coal stream C without cutting a sample. FIG. 4C shows the swing arm about to be reversed in its direction of motion so that it will move counterclockwise. However, now the sampling bucket 18 has been rotated in a clockwise direction from the position shown in FIG. 4B, thereby locating its inlet 18B so as to cut a sample from the free falling coal stream C. As the swing arm reaches the home position shown in FIG. 4D, the sampling bucket 18 will be rotated clockwise while the directing means 28 will be moved in a counterclockwise direction so as to pass below the bucket 18 and be in a position to receive the coal sample and direct it over the means 28 and through the shield 34 as seen in FIG. 2. The last referred to sequence of motions is illustrated in FIG. 4E.

Referring to FIG. 1, there is shown at 40 an electrical control box which carries on its front face selector knobs or dials which will be referred to presently. Next to the box 40 is another box 41 which contains all of the necessary hydraulic control relays and other elements which will be described in connection with the hydraulic circuit diagram seen in FIG. 5. There is also shown in FIG. 1, motor means 42 which is positioned on the hydraulic fluid reservoir 43, and the motor drives a hydraulic pump which is obscured by the motor 42 in this view. Hydraulic lines run from the pump through the controls in the box 41, and then to the hydraulic motors which will be hereinafter referred to as the description proceeds.

Figure 5:
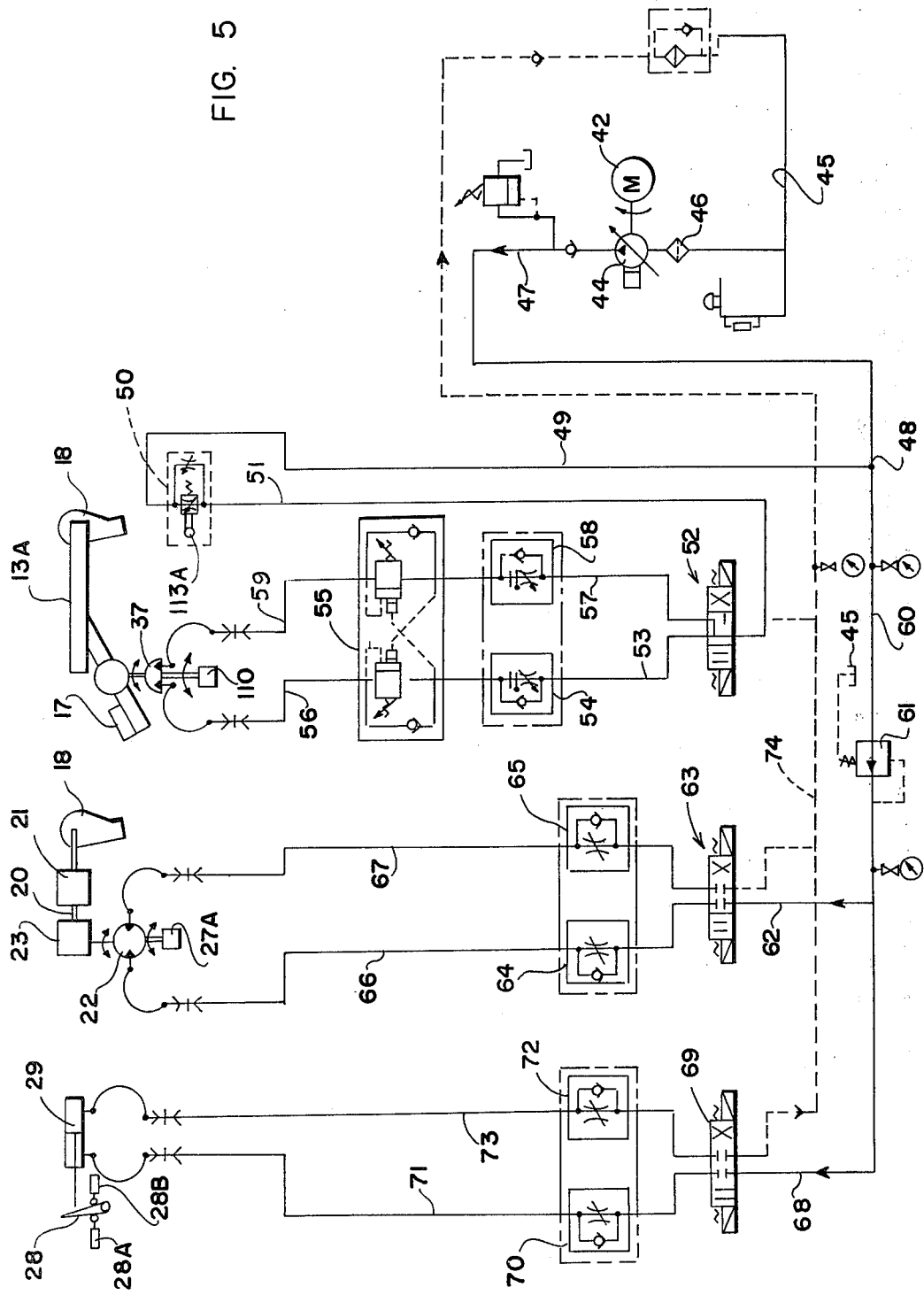
FIG. 5 is a schematic diagram of the hydraulic drive system for the swing arm, for the sampling bucket, and for the deflector associated with the sampling bucket.

Referring now to FIG. 5, the hydraulic circuit diagram includes the hydraulic pump 44 which is driven by motor 42 so as to draw the hydraulic fluid from the reservoir 45 through a suitable filter 46, and the hydraulic fluid is then delivered through line 47 to a junction 48. The hydraulic line 49 from the junction 48 is directed through a deceleration valve 50 which is operated by cam means responsive to the swing arm motion for controlling the speed of the swing arm at certain times during its range of motion. Conduit 51 extends from the deceleration valve 50 to a four-way solenoid controlled valve 52 which is normally spring centered. The valve 52 is normally set so that hydraulic fluid passes through the left hand conduit 53 and through a flow control valve 54 on its way to a counterbalance valve set 55 before passing through the conduit 56 and to the left hand inlet for oscillating actuator 37 previously referred to in FIG. 2. The counterbalance valve set 55 is provided to allow pressure fluid supply to the oscillating actuator 37 but responds to prevent loss of pressure fluid should the system in advance of the valve set 55 malfunction. Therefore, the valve set 55 will operate to retain pressure fluid between it and the actuator 37 so that the swing arm will remain in a given position. When it is desired to reverse the motion of the swing arm, the four-way valve 52 is shifted by its solenoid so that pressure fluid will pass through the conduit 57 and through an associated speed control means 58 which is manually set as desired. Pressure fluid will then pass through the counterbalance set 55 and into conduit 59 which is connected to the right hand side of the oscillating actuator 37 for the purpose of moving the swing arm in an opposite direction.

Returning to the pressure fluid junction 48, a branch conduit 60 is connected to a pressure reducing valve 61 because high pressure hydraulic fluid is not necessary for actuating the sampling bucket or the deflector gate. In this case, pressure fluid flows through branch conduit 62 to a four-way solenoid actuated valve 63 which is spring retained in its neutral position and solenoid operated in either direction so as to supply pressure fluid either through manual flow control means 64 or a similar control means 65. Conduits 66 and 67 will then supply pressure fluid to one or the other sides of a reversible hydraulic motor 22 which has been previously referred to in FIG. 3. The motor 22 operates a reduction gear unit 23 at the inner end of the swing arm 13A for the purpose of driving a torque shaft 20 which is connected to a second gear reducer 21 associated directly with the sampling bucket 18.

The branch conduit 60 also supplies hydraulic fluid through conduit 68 to a four-way solenoid control valve 69 which is normally spring centered in a neutral position and solenoid operated in either direction for directing pressure fluid through either manual flow control means 70 and into conduit 71 or manual control means 72 and into conduit 73. The pressure fluid in conduit 71 is directed into the hydraulic cylinder 29 for moving the directing means 28 out of the path of movement of the sampling bucket 18. When pressure fluid is supplied to conduit 73, it enters the cylinder 29 and moves the means 28 under the sampling bucket 18 so as to direct the coal sample as desired when the bucket is rotated into its dump position as depicted in FIG. 4E. A hydraulic flow return conduit 74 connects the respective four-way valves 52, 63 and 69 to the reservoir 45.

Figure 6:
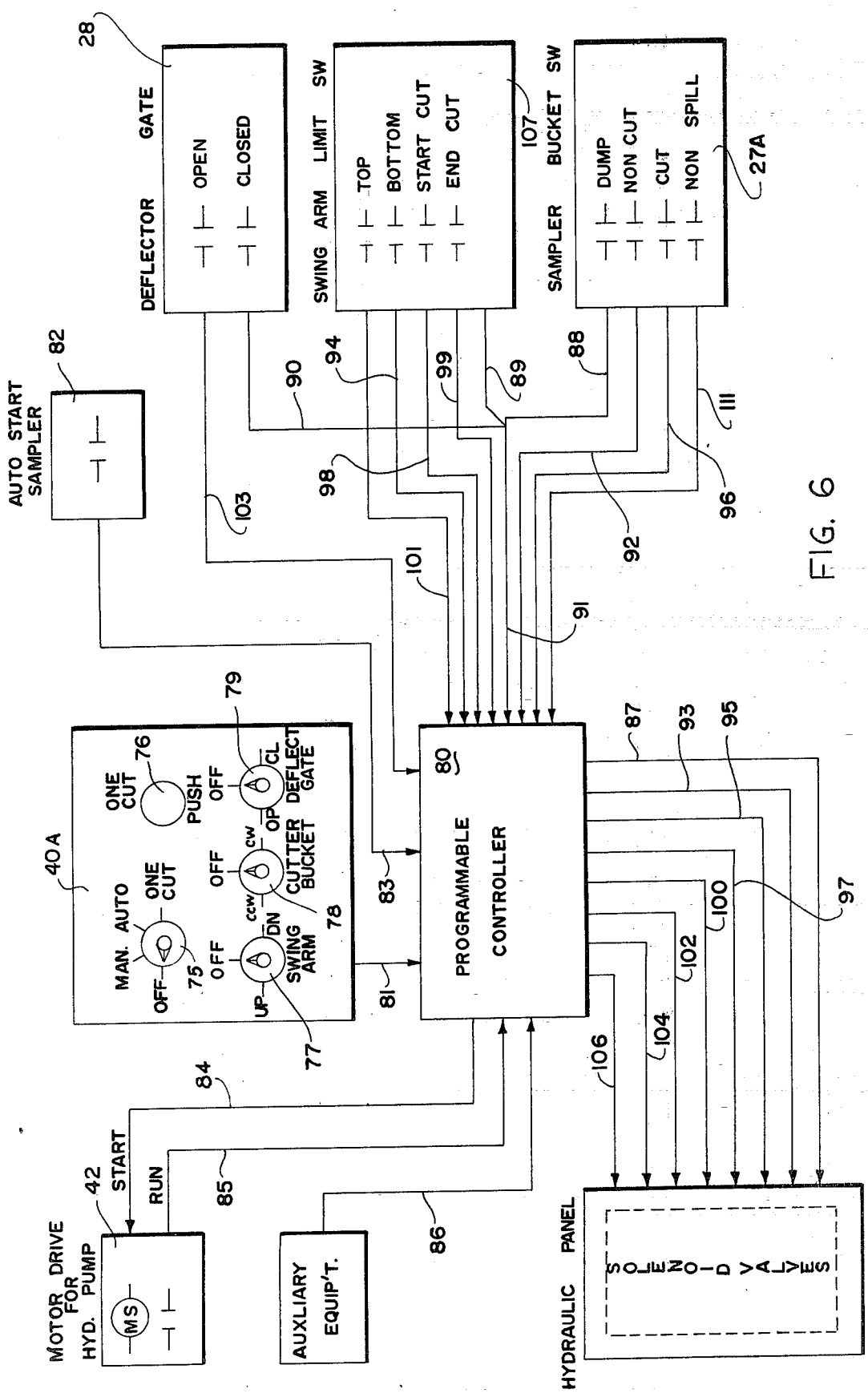
FIG. 6 is a logic diagram of the electrical control system associated with the operating components depicted in the several views of the drawings.

Reference will now be made to FIG. 6 where there is shown a logic diagram of the electrical control system. In this view, the panel 40A on the control box 40, previously referred to in FIG. 1, is provided with a selector switch 75 which is rotatable from an off position to any one of three other positions indicated for selecting manual operation of the swing arm apparatus, automatic operation thereof, or operation to perform a single sampler cut through the coal stream. There is provided a push button control 76 which will initiate the "one cut" swing arm operation. If the manual operation is selected at switch 75, then the operator may control the selector switches 77, 78 and 79 so that the travel of the swing arm in the up or down directions can be selected, the rotational displaced position of the sampler bucket 18 can be controlled as between counterclockwise or clockwise rotation, and the extension or retraction of the directing means 28 can be regulated. Generally, the controls just described will transmit a signal into the programmable controller 80 which is mounted in the electrical control box 40. The controller 80 will respond to whichever mode of operation is associated with the signal input at lead 81. Since the swing arm sampler apparatus is under the control of the purchaser, the purchaser usually provides a control device 82 which will transmit a signal through lead 83 into the programmable controller 80. Having received the necessary signals, the controller 80 will transmit a signal through lead 84 to the starting circuit for the electric motor 42 which then operates the hydraulic pump 44. The operation of the hydraulic pump 44 will be indicated by a signal through lead 85 back to the controller 80 which will then respond. Concurrently any auxiliary equipment associated with the sampler apparatus 10 must be placed in operation and a suitable signal is transmitted by lead 86 into the controller 80 which will then respond to the signals received through leads 85 and 86 by sending a signal through lead 87 into the controls in the box 41 where a suitable signal is transmitted to rotate the sampling bucket 18 in a counterclockwise direction from the position shown in FIG. 4A to the position shown in FIG. 4B for the purpose of preparing the swing arm to move downwardly through the free fall coal stream C. However, before the sampling bucket is moved in a counterclockwise direction, the controller 80 must receive a signal in lead 89 that a switch at the housing 107 (see FIG. 2) has signaled that the swing arm is at its top position. In addition, the controller must receive a signal in lead 88 that the bucket 18 is in its dump position and a signal in lead 90 from a switch associated with the directing means 28 indicating that such means is in its retracted position as shown in FIG. 4A. These leads 88, 89 and 90 form a bundle 91. It is also to be understood that the term "lead" may not always mean a single wire strand. The controller 80 sends a signal in lead 87 to the hydraulic system of FIG. 5 to rotate the sampling bucket 18 counterclockwise into the position shown in FIG. 4B. The sampling bucket 18 having rotated into its non-cut position, seen in FIG. 4C, a signal will be transmitted through lead 92 to the controller 80 and that will then indicate to the controller that it is proper to transmit a signal through lead 93 to the hydraulic control system to initiate the swinging motion of the arm into the down position indicated in FIG. 4C. When the arm reaches its bottom position, a contact in the means 107 will transmit a signal through lead 94 to the controller 80 signifying that the arm is now in its bottom position. This signal will be followed by the controller 80 sending a signal through lead 95 to the hydraulic control system for the purpose of having the motor means 23 rotate the sampling bucket 18 into its sample cut position which would cause the bucket 18 to rotate from the position shown in FIG. 4B to the position shown in FIG. 4C where the open mouth 18B is facing in a direction substantially parallel to the swing arm 13A. A further signal would be generated by the sampling bucket switch in housing 27 to generate a signal through lead 96 to indicate to the controller 80 that the sampling bucket 18 is in the cut position.

At this point, the programmable controller 80 will generate a signal in lead 97 to the hydraulic control system to cause the four-way solenoid valve 52 to direct the hydraulic fluid in conduit 57 such that the actuator 37 will swing the arm in its upward direction to obtain a sample cut of the coal as it moves at a substantially uniform speed through the free falling coal stream between the position shown in FIG. 4C and a position somewhat in advance of the position of the swing arm as shown in FIG. 4D. Subsequent to the upward movement of swing arm 13A, a signal which indicates the start of a cut will be generated from the switch in means 107 to be transmitted through lead 98 to the controller 80. The swing arm will continue to move and when it reaches the position shown in FIG. 4D, a signal in lead 99 will signify to the controller 80 that the swing arm is in its position ending the cut of a sample. The signals from leads 98 and 99 are used with timing circuits in controller 80 to determine the elapsed time of the swing arm through the stream, this timing determines the speed of travel for adjusting swing arm travel speed. The controller 80 will then respond by transmitting a signal through lead 100 to the hydraulic control system to cause the motor 22 to rotate the sampling bucket 18 in a clockwise direction from the position shown in FIG. 4C to the position shown in FIG. 4D where the bucket will rest in a non-spill position. The controller 80 must receive a signal through lead 101 from switch 107 to indicate that the swing arm is at the top or home position, at which time, a signal from the controller 80 in lead 102 will be transmitted through the hydraulic control system to the cylinder actuator 29 to move the directing means 28 into the extended position shown in FIG. 4E.

It is shown in the circuit of FIG. 6 that a signal in lead 103 is received by the controller 80 when the directing means 28 is extended for the purpose of receiving the sample of coal from the sampling bucket 18. The response of the controller 80 to the signal from lead 103 is to send a signal through lead 104 to the cylinder 29 for rotating the sampling bucket 18 into the position of FIG. 4E for dumping the coal sample. A signal from the switch 27A in housing 27 will be transmitted through lead 88 to the controller 80 signifying that the sampling bucket 18 is in its dump position. After the bucket has had time to dump, the controller 80 transmits a signal through lead 106 to the hydraulic control system to actuate the cylinder 29 to move the directing means 28 into its retracted position shown in FIG. 4A where it is out of the path of the next movement of the swing arm and sampling bucket 18 in the direction to pass through the free falling stream C of coal.

There is shown in FIG. 2 a rotary position switch 107 operated by a pulley 108 in the housing 36, and pulley 108 is driven by a belt 109 from a pulley which rotates with the shaft 15 for moving the swing arms 13A and 13B. The pulley is not shown because it is behind a cam 110 which has a suitable profile for operating the deceleration valve 50 (see FIG. 5). While a pulley and belt drive has been shown, it is understood that any suitable drive can be employed. As indicated in FIG. 6, the position switch 107 at housing 36 has a number of contacts which monitor the movement of the swing arm and generate signals in the respective leads 89, 94, 98, 99 and 101 corresponding to the swing arm positions illustrated in FIGS. 4A to 4D.

In a similar manner, the housing 27 (see FIG. 2) contains a rotary position switch 27A (see FIG. 5) which is operated from the reduction gear 23 driven by the hydraulic motor 22. This switch 27A has suitable contacts for monitoring the position of the sampling bucket 18 and generating signals in leads 91, 92, 96 and 111, corresponding to the sampling bucket 18 in its dump position (FIG. 4E), in its non-cut position (FIG. 4B), in its sample cut position (FIG. 4C), and on its non-spill position (FIG. 4D).

The views of FIGS. 5 and 6 indicate the presence of position switches 28A and 28B associated with the directing means 28 for generating signals in leads 90 and 103 for transmittal to the controller 80.

In the view of FIG. 2, the conveyor belt B brings the material to be sampled into the apparatus 10 at the head pulley P where it is released in a free falling stream C. The path of the stream C is dependent upon the velocity of the conveyor belt B, that is to say, the stream may fall almost directly off the pulley P, or it may be accelerated and follow a curved path farther out from the pulley P. What has been illustrated in FIG. 2 is an average path for the stream. Once the velocity of the belt B is known, it is possible to calculate the necessary velocity of the sampling bucket 18 in the distance from the point of starting to cut a sample to the point of conclusion of the cut. In this distance, the bucket velocity should be uniform, and thereafter, the velocity can decelerate. The bucket velocity can be regulated by measuring the hydraulic fluid flow into the oscillating actuator 37 in terms of gallons per minute which can be translated into bucket velocity in feet per second. The importance of obtaining a uniform or constant bucket velocity during the sample cutting movement is one of the requirements of the American Society of Testing Materials. The bottom position for the sampling bucket 18 prior to cutting a sample is close to the path of the stream of falling material while the path of travel between the end of the sample cut and the home position is much longer. It thus becomes necessary for the swing arm 13A to get the sampling bucket 18 up to the desired or predetermined velocity quickly and then hold that velocity substantially constant before decelerating to zero velocity at the home position. The purpose for the valve 50, which is controlled by the cam 113 engaging the cam follower 113A (FIG. 5), is to assure the desired velocity performance of the swing arm 13A.

It is important to provide a sampling bucket 18 with a mouth 18B sized to the particle size of the material in the falling stream, as it makes a difference in what quantity of material is being cut from the falling stream. The velocity of the bucket, size of mouth, and number of samples to be obtained in a given time span is dependent on ASTM standards.

OPERATION

The operation of the described embodiment is best understood from the disclosure in FIGS. 5 and 6 showing the drive control arrangement for the swing arm (hereinafter designated 13A), and the pivotally mounted sampling bucket carried by the swing arm.

The hydraulic fluid pump 44 supplies pressure fluid through a deceleration control valve 50 to a four-way solenoid controlled flow reversing valve 52 connected to the rack and pinion actuator 37 for moving the swing arm 13A between its home position (FIG. 4A) and its bottom position (FIG. 4C). The pressure fluid is also supplied to the four-way solenoid controlled flow reversing valves 63 and 69 connected respectively to the reversible hydraulic motor 22 which pivots the sampling bucket 18 in a predetermined manner responsive to the electrical control circuit arrangement of FIG. 6, and to the pressure fluid actuator 29 which moves the deflector gate 28 between its retracted position (FIG. 4A) and its operative deflecting position (FIG. 4E).

The electrical control circuit is arranged to run the hydraulic fluid pump 44 and to receive a signal that any essential operative accessory devices are operating in response to outside controls independent of the present arrangement. When the pump 44 is operative, and the outside devices signal operative conditions, a programmable controller 80 contained in the control circuit coordinates the operative functions of the swing arm 13A, the pivotal position desired for the sampling bucket 18, and the retracted and operative positions for the means 28. These operating components of the apparatus, when operating in an automatic or in a one-cut cycle, follow predetermined responses contained in the programmable controller 80. For example, when the swing arm 13A is to be moved through the falling coal stream C from its home position, the sampling bucket 18 must be rotated in a counterclockwise direction from the position shown in FIG. 4A to the position in FIG. 4B before the swing arm 13A begins its clockwise movement toward the position shown in FIG. 4C. It is necessary that the sampling bucket 18 be pivoted in this manner so that its rounded closed end 18A will be presented to the free falling stream C, thereby not cutting a sample from said stream. When the swing arm 13A has reached its bottom position, as in FIG. 4C, the controller 80 will receive a signal of the swing arm 13A position and transmit a suitable signal to the valve 63 for rotating the sampling bucket 18 clockwise into the position shown in FIG. 4C where the mouth 18B will be directed along the swing arm 13A so that a signal will then be received by the controller 80 to reverse the actuator 37 through its flow reversing valve 52 to move the swing arm 13A through the free falling stream C and into the position shown in FIG. 4D. In the latter movement of the swing arm 13A after it has cut a sample of the free falling material, it must be rotated in a further clockwise direction to assume a position where the sample that has been collected will not be spilled. The specific non-spill position of the sampling bucket 18 is shown in FIG. 4D. The attainment of the swing arm 13A in its return to the home position will transmit a signal to the controller 80 which will signal the valve 69 to move the directing means to its operative position of FIG. 4E so that a sample dumped from the bucket 18 will be directed in the proper direction through the means 34 for further processing. The controller 80 will then receive a signal which will cause the reversing motor means 22 to move the bucket 18 into its dump position.

It should be evident from the foregoing that the drive control arrangement for the swing arm sampler apparatus, having a pivotal sampling bucket moved by the swing arm in opposite directions through a free falling stream of material to be sampled from a home position at one side of the falling stream, comprises an electrically operated driven hydraulic fluid pump 44, a reversible hydraulic fluid motor 37 connected to the swing arm 13A, a second reversible hydraulic fluid motor 22 connected to the sampling bucket 18, and a hydraulic fluid circuit containing the hydraulic fluid pump 44, and the first and second hydraulic fluid motors 37 and 22, and wherein the hydraulic fluid circuit includes electrically controlled fluid flow reversing valves 52 and 63 associated with the first and second hydraulic fluid motors. The drive control arrangement further comprises first electrical switches connected to monitor the movement of the swing arm 13A for generating signals at predetermined positions of movement thereof, second electrical switches responsive to the pivotal movement of the sampling bucket 18 when monitoring that movement and to generate signals in predetermined positions of pivotal movement thereof. An electrical control circuit is provided for containing the foregoing electrical switches, the electrically controlled flow reversing valves, and the electrical motor drive for the fluid pump, wherein the control circuit provides a programmable controller for initiating operation of the hydraulic fluid pump and for responding to the signals generated by the monitoring function of the first and second electrical switches, such that the program in the controller is effective for governing the movement of the swing arm 13A and the pivoting of the bucket 18 relative to the swing arm throughout the operation of obtaining a sample from the free falling stream and dumping it at the directing means 28 so that it may be moved through further processing equipment.

Having described what is presently included in a preferred embodiment, it should now be apparent to those skilled in the pertinent art that modifications in arrangement and detail may come to mind without departing from the principles of the invention which have been illustrated in the accompanying drawings.

What is claimed is:

1. A drive control arrangement for swing arm sampling apparatus having a pivotal sampling bucket moved by the swing arm in opposite directions through a free falling stream of material to be sampled from a home position at one side of the falling stream, said drive control arrangement comprising:
   electrical motor driven hydraulic fluid pump means;
   first reversible hydraulic fluid motor means connected to said swing arm;
   second reversible hydraulic fluid motor means connected to said sampling bucket;
   hydraulic fluid circuit means containing said hydraulic fluid pump and said first and second reversible hydraulic fluid motor means, including electrically controlled hydraulic fluid flow reversing valve means in said fluid circuit means for said first and second hydraulic fluid motor means;
   first electrical switch means connected to said swing arm for actuation by said swing arm in predetermined positions of movement thereof;
   second electrical switch means connected to said pivotal sampling bucket for actuation by said bucket in predetermined positions of pivotal movement thereof;
   and electrical control circuit means containing said first and second electrical switch means, said electrically controlled fluid flow reversing valve means, and said electrical motor drive;
   said electrical control circuit means including a controller for initiating operation of said hydraulic fluid pump means and for responding to first and second electrical switch means;
   said controller being programmed for effecting the movement of said swing arm and the pivoting of said sampling bucket relative to said swing arm in obtaining a sample from the free falling stream.

2. A drive control arrangement according to claim 1 wherein said first electrical switch means is responsive to said first reversible hydraulic fluid motor means.

3. A drive control arrangement according to claim 1 wherein said second electrical switch means is responsive to said second reversible hydraulic fluid motor means.

4. A drive control arrangement according to claim 1 wherein said hydraulic fluid circuit contains said hydraulic fluid pump, said first reversible hydraulic fluid motor means and said electrically controlled hydraulic fluid flow reversing valve means includes fluid flow decelerating means.

5. A drive control arrangement according to claim 1 wherein means for preventing loss of hydraulic fluid is included in said hydraulic fluid circuit in cooperation with said first reversible hydraulic fluid motor means connected to said swing arm.

6. A drive control arrangement according to claim 1 wherein hydraulic flow control means is included in said hydraulic fluid circuit in cooperation with said second reversible hydraulic fluid motor means connected to said sampling bucket.

7. A drive control arrangement for a swing arm material sampling apparatus having a pivotal material sample collecting bucket moved by the wing arm between a home position and a sampling start position and a directing means in the home position for directing the dumping of the collected sample of material, said drive control arrangement comprising:
   hydraulic fluid pump means;
   reversible hydraulic motor means for each of the swing arm, the sample collecting bucket and the directing means;

hydraulic fluid circuit means containing said hydraulic pump means and each of said reversible hydraulic motor means, including a fluid flow reversing means in the fluid circuit for each of said hydraulic motor means;

electrically operated switch means responsive to the movement of said swing arm, to the pivotal position of said sample collecting bucket and to the movement of said directing means;

and electrical control circuit means containing said electrically operated switch means, and including solenoid means operatively connected to each of said fluid flow reversing means for said hydraulic motor means;

said electrical control circuit means also including a programmable controller for initiating operation of said hydraulic fluid pump means, and for operating said solenoid means in response to the switch means;

said programmable controller determining the sequence of operation of said swing arm, said sample collecting bucket and said directing means.

8. A drive control arrangement for a swing arm coal sampling apparatus having a pivotal coal sample collecting bucket moved by the swing arm between a home position and a coal sampling start position, said drive control arrangement comprising:

hydraulic fluid pump means;

reversible hydraulic motor means connected to each of the swing arm and the coal sample collecting bucket;

hydraulic fluid circuit means containing said hydraulic fluid pump and each of said reversible hydraulic motor means, including hydraulic fluid flow reversing means in said fluid circuit for each of said reversible hydraulic motor means;

electrically operated switch means responsive to the positions of said swing arm and to the pivoting of said coal sampling bucket;

and electrical control circuit means containing said hydraulic flow reversing means, said reversible hydraulic motor means for each of said swing arm and coal sample collecting bucket, and said switch means;

said electrical control circuit means including a controller for initiating operation of said hydraulic fluid pump means to deliver hydraulic fluid to said fluid flow reversing means, for operating said fluid flow reversing means, and for monitoring said switch means;

said controller being programmed for operating said fluid flow reversing means in response to the monitoring of said switch means, whereby said swing arm and said bucket cooperate in obtaining a coal sample.

* * * * *

UNITED STATES PATENT AND TRADEMARK OFFICE
CERTIFICATE OF CORRECTION

PATENT NO. : 4,326,425

DATED : April 27, 1982

INVENTOR(S) : Ray S. Gundersen, Ronald J. Colledge, Roy H. Jenkins and Michael Crook It is certified that error appears in the above-identified patent and that said Letters Patent are hereby corrected as shown below:

Column 7, line 43, "on" should be --- in ---.

Column 10, line 60, "wing" should be --- swing ---.

Signed and Sealed this

Sixth Day of July 1982

[SEAL]

Attest:

Attesting Officer

GERALD J. MOSSINGHOFF

Commissioner of Patents and Trademarks